United States Patent [19]
Brooks et al.

[11] Patent Number: 5,658,349
[45] Date of Patent: Aug. 19, 1997

[54] PROSTHETIC JOINT SYSTEM FOR BONE REPLACEMENT

[75] Inventors: Caleb Emerson Brooks, Town of Mt. Royal; Jan Janusz Krygier, St. Constant; John Dennis Bobyn, Montreal West, all of Canada; Alfred F. DeCarlo, Jr., Stamford, Conn.

[73] Assignee: Joint Medical Products Corporation, Stamford, Conn.

[21] Appl. No.: 185,914

[22] PCT Filed: Jul. 29, 1991

[86] PCT No.: PCT/US91/05358

§ 371 Date: Jan. 27, 1994

§ 102(e) Date: Jan. 27, 1994

[87] PCT Pub. No.: WO93/02641

PCT Pub. Date: Feb. 18, 1993

[51] Int. Cl.$^6$ .................... A61F 2/30; A61F 2/28
[52] U.S. Cl. ............................ 623/23; 623/18
[58] Field of Search .................. 623/16, 18, 19, 623/20, 22, 23

[56] References Cited

U.S. PATENT DOCUMENTS

| | | |
|---|---|---|
| 4,718,916 | 1/1988 | Morscher . |
| 4,728,335 | 3/1988 | Jurgutis . |
| 4,790,852 | 12/1988 | Noiles . |
| 4,846,839 | 7/1989 | Noiles . |
| 4,908,032 | 3/1990 | Keller ............................ 623/23 |
| 4,944,759 | 7/1990 | Mallory et al. ................. 623/23 |
| 4,997,448 | 3/1991 | Filer . |
| 5,002,578 | 3/1991 | Luman ........................... 623/23 |
| 5,026,399 | 6/1991 | Englebrecht et al. . |

FOREIGN PATENT DOCUMENTS

| | | |
|---|---|---|
| 204919 | 12/1986 | European Pat. Off. . |
| 0204919 | 12/1986 | European Pat. Off. ............ 623/22 |
| 0243298 | 10/1987 | European Pat. Off. ............ 623/23 |
| 0241846 | 10/1987 | European Pat. Off. ............ 623/23 |
| 0257359 | 3/1988 | European Pat. Off. ............ 623/23 |
| 359485 | 3/1990 | European Pat. Off. . |
| 2614524 | 11/1988 | France ........................... 623/22 |
| 2675042 | 10/1992 | France ........................... 623/23 |
| 3340767 | 5/1985 | Germany ........................ 623/22 |
| 3338314 | 7/1985 | Germany ........................ 623/22 |
| 3535158 | 4/1987 | Germany ........................ 623/22 |
| 3605630 | 9/1987 | Germany . |
| 4320086 | 12/1994 | Germany ........................ 623/23 |
| 2153233 | 8/1985 | United Kingdom ............... 623/22 |
| 9118563 | 12/1991 | WIPO ........................... 623/23 |

OTHER PUBLICATIONS

"Link Endo–Model Total Femur Replacement," Link America, Inc., East Hanover, New Jersey, 1989.

"The Leinbach Horizontal Platform Femoral Component", Allo Pro Corporation, St. Petersburg, Florida, 1982.

Primary Examiner—David Isabella
Attorney, Agent, or Firm—Maurice M. Klee

[57] ABSTRACT

A prosthetic joint system is provided for use when replacement of bone is required. The system includes an elongated stem having a joint motion surface at one end and an outside surface which includes at least one tapered portion, a sleeve for fixation to the patient's bone which has an internal taper for locking engagement with the at least one tapered portion, and a bone replacement element which can be a bone graft. The system includes means for attaching the bone replacement element to the stem at a location between the joint motion surface and the sleeve. In the case of bone grafts, the system can include a second sleeve for implantation in the graft and a second tapered portion on the stem for locking engagement with the second sleeve. Preferably, a series of mating stems, sleeves, and bone replacement elements, or second sleeves in the case of bone grafts, are provided.

19 Claims, 4 Drawing Sheets

FIG. 1.
PRIOR ART
FIG. 2.
PRIOR ART
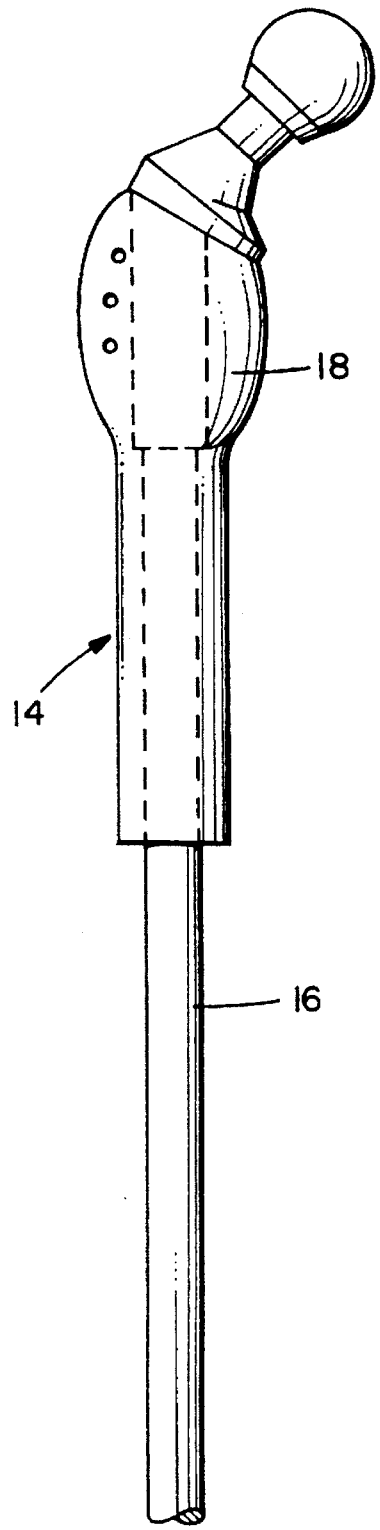
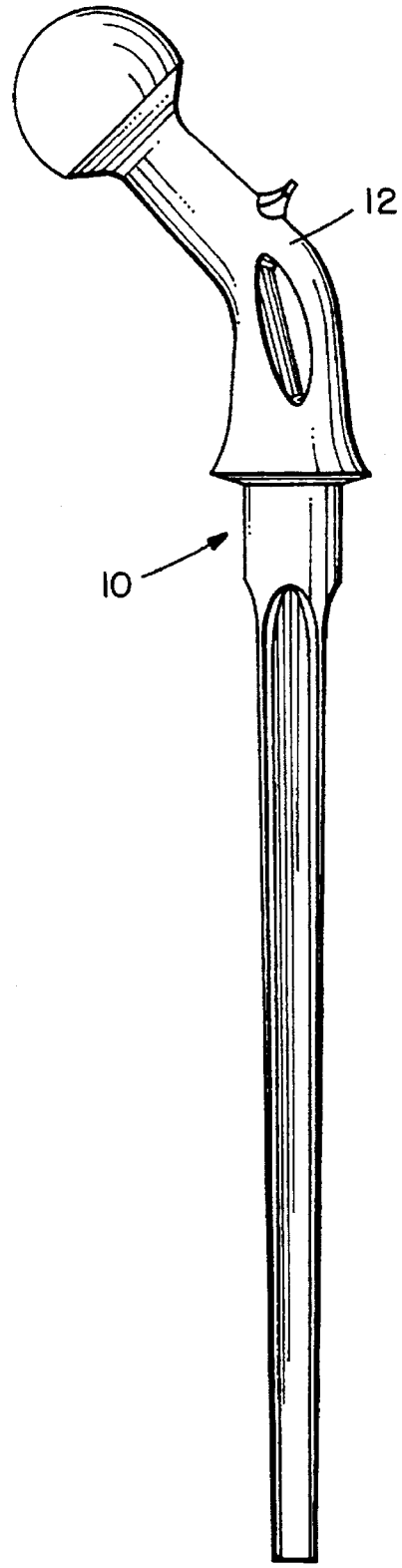

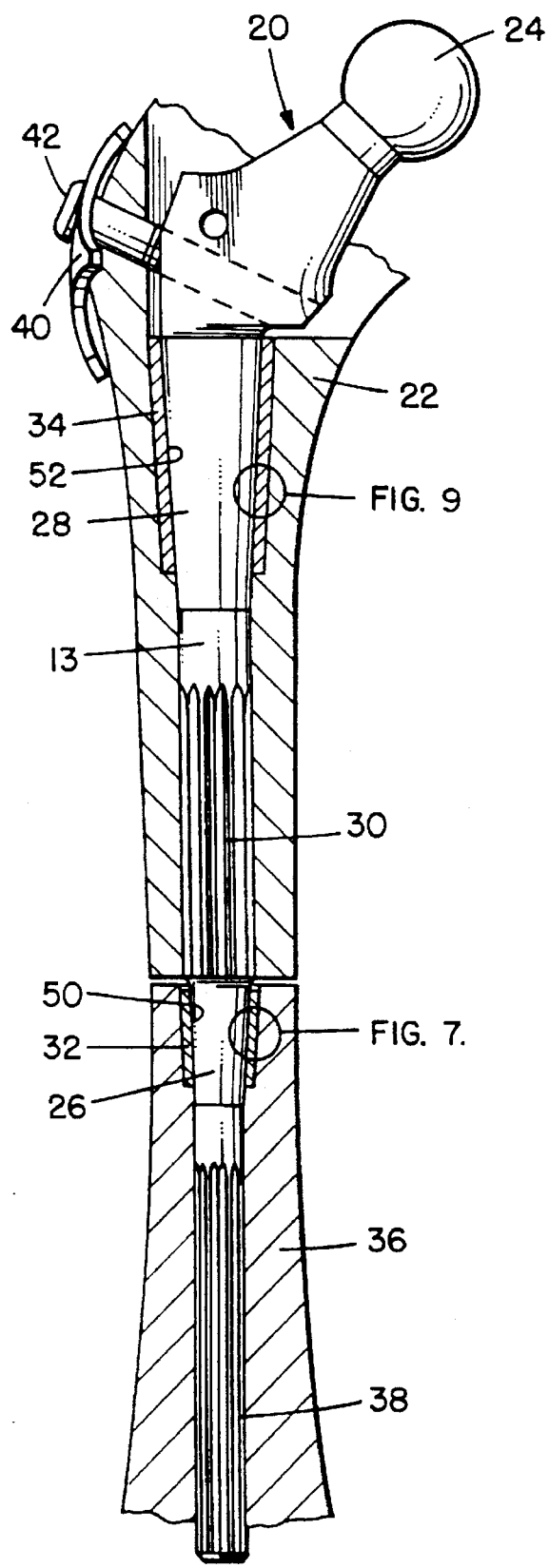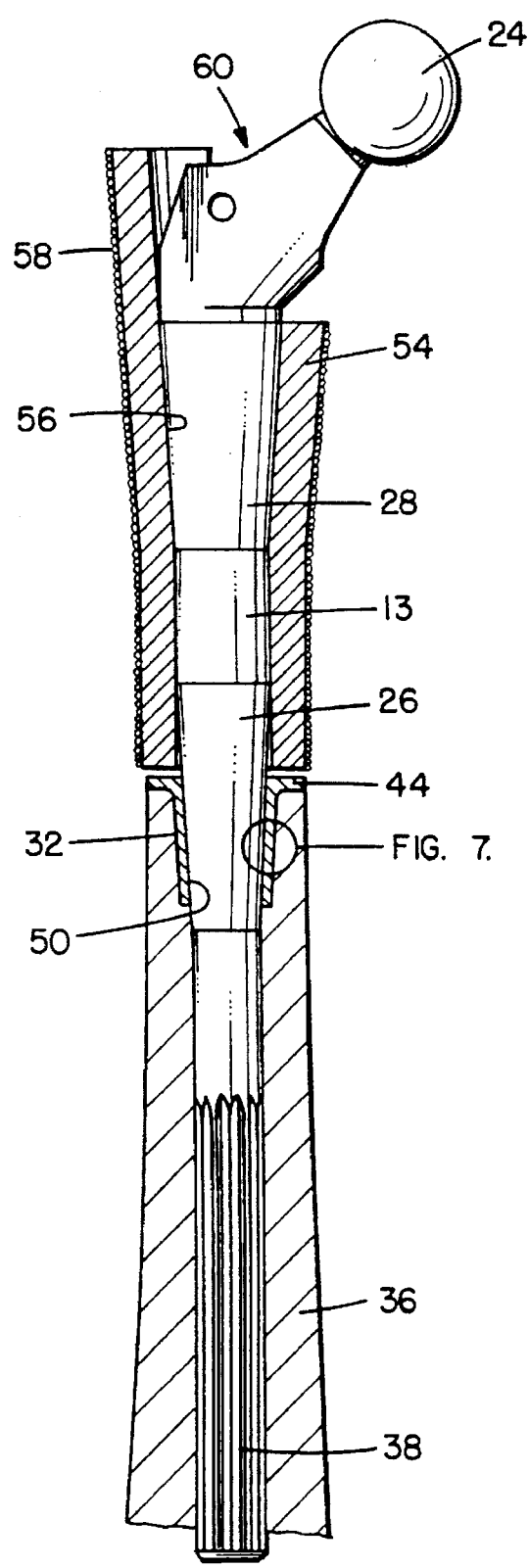

FIG. 5.
FIG. 6.
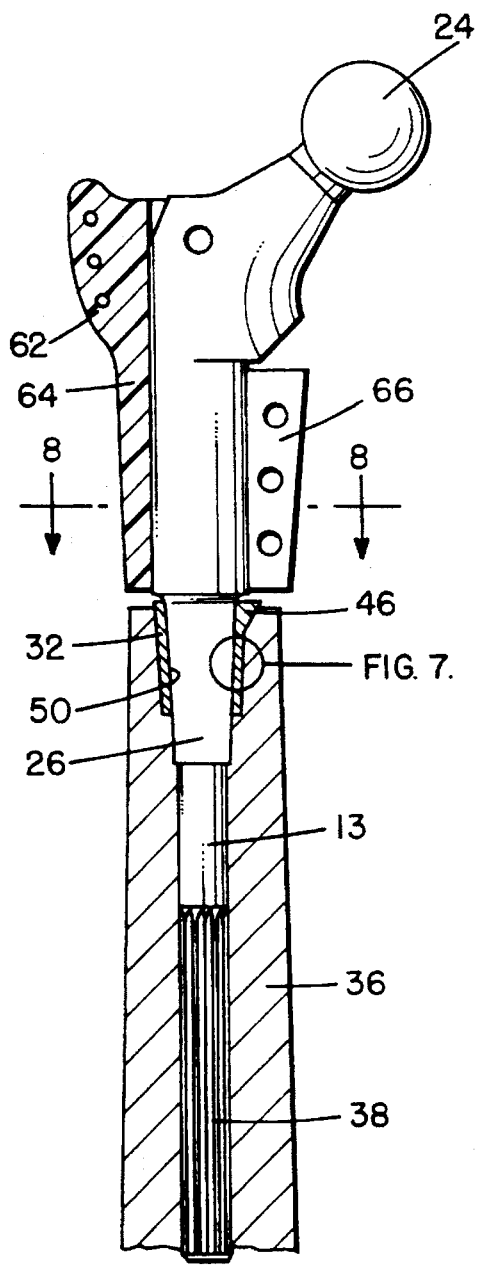
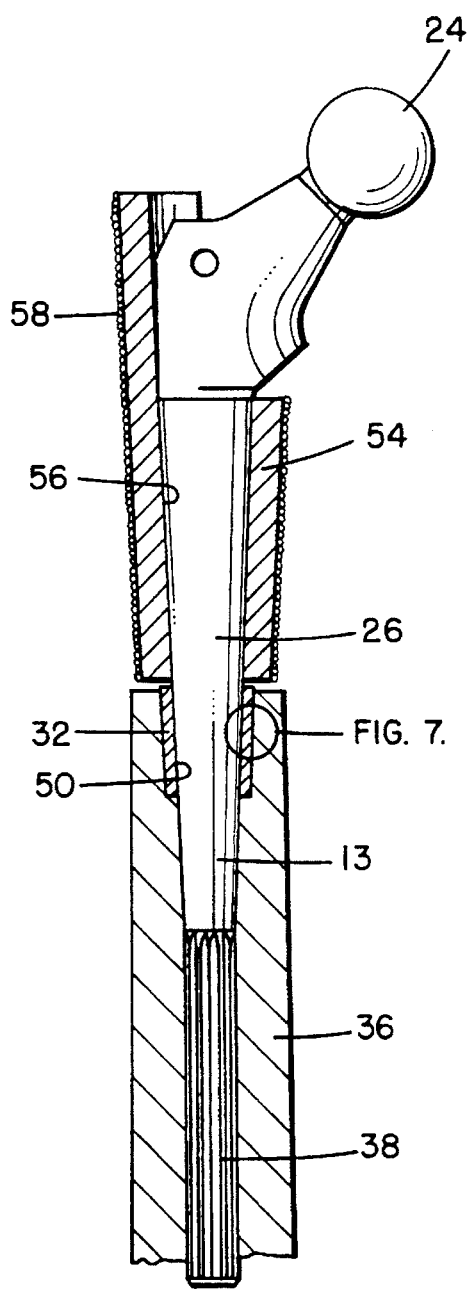
FIG. 7.
FIG. 8.
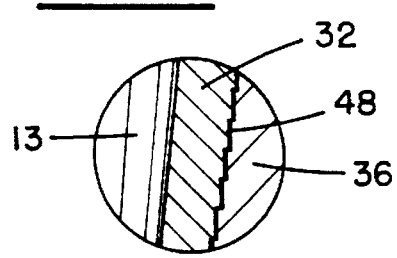
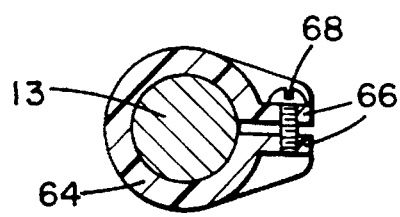

PROSTHETIC JOINT SYSTEM FOR BONE REPLACEMENT

BACKGROUND OF THE INVENTION

1. Field of the Invention

This invention relates to prosthetic joints and, in particular, to a prosthetic joint system for use when bone replacement is required.

2. Description of the Prior Art

Various prosthetic joints are known which include means for replacing bone which the patient has lost as a result of disease, trauma, or bio-mechanical degeneration caused by, for example, a previous joint implant.

FIG. 1 shows a two piece prosthesis 14 of this type which includes a stem 16 and a bone replacement portion 18 which can be a bone graft or a shaped part composed of a plastic material, such as ultra high molecular weight polyethylene (UHMWPE). See "Link Endo-Model Total Femur Replacement", Link America, Inc., East Hanover, N.J., 1989, and "The Leinbach Horizontal Platform Femoral Component", Allo Pro Corporation, St. Petersburg, Fla., 1982.

FIG. 2 shows another prior art construction of this type which comprises a one piece metal prosthesis 10 which includes a proximal portion 12 which serves as a replacement for bone. Examples of prostheses of this general type include those sold by Howmedica under the product designations "Universal 32 mm Proximal Femur Total Hip Components with Polished Loops", "Muller Type 32 mm Proximal Femur", "Harris Calcar Replacement 32 mm Total Hip System", and "Averett Modified Head Neck 32 mm Total Hip System", and those sold by DePuy under the product designation "1031-30/44 Femoral Upper Third".

Although these prostheses have benefited many patients, problems have remained with their use. In particular, with reference to the prostheses of the type shown in FIG. 2, custom prostheses are often needed and even when customized, these prostheses may not fit the patient particularly well, especially in connection with achieving a tight fit between the prosthesis and the patient's bone. These prostheses provide the surgeon with only one choice of replacement at the time of surgery which limits the ability of the surgeon to respond to specific needs or problems ascertained after the surgery has begun. Also, custom prostheses take a substantial amount of time to fabricate and are expensive.

With reference to the prostheses of the type shown in FIG. 1, these can provide the surgeon with some degree of choice at the time of surgery. Typically, a family of stems and a corresponding family of replacement portions 18 are provided to the surgeon. Also, in some cases, parts of the replacement portion can be cut away at the time of surgery to accommodate different amounts of bone loss. See the Allo Pro system, supra. However, these prostheses still suffer from problems in achieving an optimum interface between the stem 16 and the patient's bone. In particular, because of the mechanical configuration of the prosthesis, porous coating of the stem to achieve long term fixation through bone ingrowth is inadvisable since it may reduce the endurance strength or the stem.

Femoral prostheses which include sleeves for engagement with bone are also known in the art. See, for example, Noiles U.S. Pat. No. 4,846,839 and Noiles U.S. Pat. No. 4,790,852. Such prostheses have not included separate bone replacement elements of the type shown in FIG. 1 but in some cases have included an integral bone replacement portion of the type shown in FIG. 2.

SUMMARY OF THE INVENTION

In view of the foregoing state of the art, it is an object of the invention to provide improved joint replacement prostheses having bone replacement means. In particular, it is an object of the invention to provide a modular system whereby the surgeon can select the set of components most suitable to the patient's condition as determined at the time of surgery.

It is a further object of the invention to provide prostheses of the foregoing type having an improved interface between the prosthesis and the patient's bone. In particular, it is an object of the invention to provide a prosthesis employing a sleeve for engagement with the bone and a stem which interlocks with the sleeve. In this way, the sleeve can be optimized for size, shape, and surface characteristics vis-a-vis bone engagement without structurally comprising the overall strength of the prosthesis.

It is an additional object of the invention to provide improved means for attaching a bone graft or other bone replacing material to a bone replacement prosthesis which again allows selection of the optimum components at the time of surgery.

To achieve the foregoing and other objects, the invention provides a prosthesis for implantation in bone which comprises:

(a) a stem which has (i) a joint motion surface, e.g., a ball, at one end, and (ii) an outside surface which extends away from the joint motion surface and includes at least one tapered portion;

(b) a sleeve for fixation to the patient's bone which includes an internal taper for locking engagement with the at least one tapered portion of the stem;

(c) a bone replacement element; and (d) means for attaching the bone replacement element to the stem at a location between the joint motion surface and the sleeve.

In certain embodiments of the invention, the means for attaching the bone replacement element to the stem comprises an internal locking taper which engages either a part of the same tapered portion of the stem which the sleeve engages or a separate tapered portion of the stem.

The bone replacement element can be composed of various materials including bone, metal, plastic, and ceramic. When the material is bone, e.g., when the bone replacement element is a bone graft, the means for attaching preferably comprises a second sleeve which is affixed to the bone graft and has an internal taper for locking onto the stem. Also, when used with a bone graft, the stem preferably includes two tapered portions and a fluted portion between the tapered portions which engages and cuts into the graft.

The sleeve(s) are preferably stepped and may be porous coated. Also, for bone replacement elements composed of metal, the outside surface of the element may be porous coated to aid in the attachment of muscles, tendons, and other tissues.

To allow the surgeon to optimize the match between the prosthesis and the patient's specific requirements, families of stems and sleeves, and for certain embodiments, bone replacement elements, are provided to the surgeon in the operating room. In this way, the surgeon can select those components which together provide the best overall fit and function for the particular conditions presented by the patient.

The accompanying drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention.

BRIEF DESCRIPTION OF THE DRAWINGS

FIG. 1 is a side view of a prior art femoral prosthesis which includes a stem and a bone replacement portion.

FIG. 2 is a side view of a prior art femoral prosthesis whose proximal portion has been configured to replace lost bone.

FIG. 3 is a side view, partially in cross-section, of a femoral prosthesis constructed in accordance with the invention for use with a bone graft.

FIG. 4 is a side view, partially in cross-section, of a femoral prosthesis constructed in accordance with the invention having a stem with two tapered portions, one for engagement with a bone replacement element and the other for engagement with a sleeve which is implanted in the patient's femur.

FIG. 5 is a side view, partially in cross-section, of a femoral prosthesis constructed in accordance with the invention having a bone replacement element which is clamped to the prosthesis' stem and a sleeve which engages a tapered portion of the stem.

FIG. 6 is a side view, partially in cross-section, of a femoral prosthesis constructed in accordance with the invention having a stem with an elongated tapered portion for engagement with both a bone replacement element and with a sleeve which is implanted in the patient's femur.

FIG. 7 is an expanded view of the outside surface of sleeve 32 of FIGS. 3–6 illustrating the use of steps or terraces on the outside surface.

FIG. 8 is a cross-sectional view along lines 8—8 in FIG. 5 illustrating representative means for attaching a bone replacement element to the prosthesis' stem.

DESCRIPTION OF THE PREFERRED EMBODIMENTS

Figure 9:
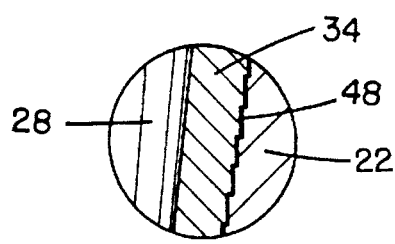
FIG. 9 is an expanded view of the outside surface of sleeve 34 of FIG. 3 illustrating the use of steps or terraces on the outside surface.

With reference now to the drawings, wherein like reference characters designate like or corresponding parts throughout the several views, there is shown in FIG. 3 a femoral prosthesis 20 constructed in accordance with the invention which incorporates bone graft 22.

Prosthesis 20 includes elongated stem 13 which has ball 24 at one end which serves as a joint motion surface. The outside surface of stem 13 includes a first tapered portion 26 and a second tapered portion 28. Between the tapered portions are flutes 30. Stem 13 also includes a second set of flutes 38.

Prosthesis 20 further includes first sleeve 32, second sleeve 34, and trochanter washer 40 which is attached to stem 13 by screw 42. First sleeve 32 is implanted in the patient's femur 36 and provides strong mechanical fixation of the prosthesis to the proximal end of the femur. Additional fixation of the prosthesis to the femur is provided by flutes 38 which help stabilize the distal end of the prosthesis with regard to rotation about the prosthesis' longitudinal axis.

In practice, a series (family) of sleeves 32 of different sizes and/or configurations is provided to the surgeon so that he or she can choose the sleeve which provides the best union with whatever portion of the femur remains for implantation. Similarly, a family of stems 13 is also provided to the surgeon so that again optimizing choices can be made at the time of implantation.

Figure 10:
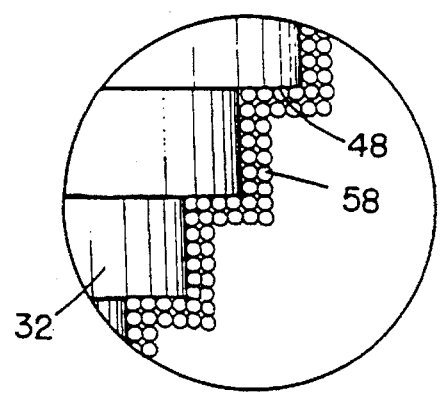
FIG. 10 illustrates the use of a porous coating on the outside surface of sleeve 32 of FIGS. 3–6.
Figure 11:
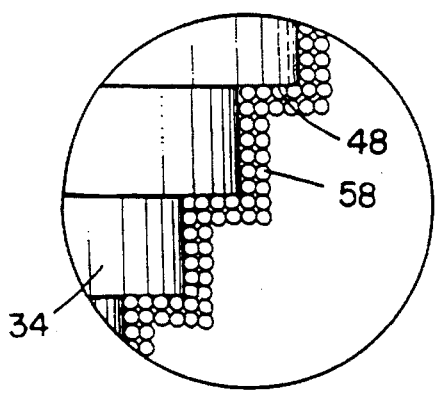
FIG. 11 illustrates the use of a porous coating on the outside surface of sleeve 34 of FIG. 3.

As shown in FIG. 7, sleeve 32 preferably has a stepped outside surface 48 of the type described in Noiles, U.S. Pat. No. 4,846,839, the relevant portions of which are incorporated herein by reference. As also described in that patent, if porous coating 58 is used, such coating is preferably applied to just the sleeve and not to the stem (see FIG. 10). In this way, an opportunity for bone ingrowth is provided without putting the overall structural integrity of the prosthesis at risk.

As shown in FIG. 4, if desired, sleeve 32 can include a collar 44 for engagement with the exposed, proximal end of the femur. Similarly, as shown in FIG. 5, the sleeve can include a protruding portion 46 constructed in accordance with Noiles, U.S. Pat. No. 4,790,852. It is to be understood, of course, that the illustrated sleeves can be used with any of the prostheses of FIGS. 4–6. Whatever construction is used for the sleeve's outside surface, its inner surface includes a tapered portion 50 for locking engagement with first tapered portion 26 of stem 13.

The prosthesis of FIG. 3 includes second sleeve 34 for engagement with bone graft 22. Depending upon the size and shape of the bone graft, sleeve 34 can include various of the features discussed above with regard to sleeve 32. Thus, it can include a collar 44, a protruding portion 46, a stepped outside surface 48, and, if desired, a porous coating 58 or other coating to enhance adhesion when cement is used to affix the graft. As with the first sleeve, whatever configuration is chosen for the outside surface of the second sleeve, its inner surface includes a tapered portion 52 for locking engagement with second tapered portion 28 of stem 13.

In addition to sleeve 34, flutes 30 and trochanter washer 40 also help affix bone graft 22 to stem 13. The sleeve serves as the primary source of mechanical fixation between the graft and the stem. The flutes provide further fixation by helping prevent rotation of the graft about the stem as torque is applied to the graft by the patient's tendons and muscles. Trochanter washer aids in the attachment of those tendons and muscles to the prosthesis and also helps stabilize and strengthen the greater trochanter portion of the graft. The combination of these three fixation mechanisms provides excellent stabilization of bone grafts including long bone grafts.

FIG. 4 shows an alternate embodiment 60 wherein a bone replacement element 54 composed of metal is used in place of bone graft 22. For this embodiment, as well as those shown in FIGS. 5 and 6, a series of bone replacements is preferably provided to the surgeon so that a selection of the most appropriate element can be made at the time of surgery.

As in FIG. 3, stem 13 includes a first tapered portion 26 which mates with first sleeve 32. The stem also includes second tapered portion 28 which mates and locks with taper 56 formed on the inside surface of element 54. As shown in FIG. 4, the outside surface of element 54 can include a porous coating 58 to aid in the integration and bonding of the prosthesis to the patient's tissues. Although not shown in FIG. 4, element 54 can also include a muscle/tendon attachment plate 62 of the type shown in FIG. 5.

FIG. 6 shows a variation of the prosthesis of FIG. 4 wherein the stem's first tapered portion 26 has been elongated so that it mates with the internal tapers of both sleeve 32 and bone replacement element 54. Such a construction can also be used with the bone graft embodiment of FIG. 3 for applications in which flutes 30 are not required.

FIG. 5 shows a further variation of the invention employing a bone replacement element 64 composed of plastic. Instead of locking tapers, this embodiment uses opposing flanges 66 and locking screws 68 to attach element 64 to stem 13. Such an attachment system can also be used with the metal bone replacement elements of FIGS. 4 and 6. Also, for a ceramic bone replacement element, the attachment system of FIG. 5 can be combined with a taper lock of the type shown in FIGS. 4 and 6 to produce a strong attachment.

The prostheses of the invention can be implanted using a variety of techniques known in the art. Trial components are typically used to select a set of components best suited to the patient's needs. The patient's femur is resected as necessary and a straight hole for receiving stem 13 is reamed into the femur's medullary canal. A conical cavity is then formed in the end of the femur for receiving sleeve 32. For sleeves including a protruding portion 46, a side cavity for that portion can be formed in the end of the femur using a cutting tool of the type disclosed in U.S. Pat. No. 4,790,852, the relevant portions of which are incorporated herein by reference.

The bone replacement element is affixed to stem 13 prior to its implantation. In the case of a metal element of the type shown in FIGS. 4 and 6, fixation can be achieved by placing the element in an appropriate fixture and then applying a sharp impact force to stem 13 to lock the complimentary tapers on the element and the stem together. For a plastic element of the type shown in FIG. 5, the element is slid over the seem and then tightened into place using screws 68.

In the case of a bone graft, a cavity for the stem and sleeve 34 can be formed in the graft using techniques similar to those used to prepare the patient's femur. Sleeve 34 is then implanted in the graft, with or without cement, and the stem and sleeve are united by applying a sharp impact force to the stem to lock together the complimentary tapers.

After the bone replacement element has been locked onto the stem, the prosthesis is inserted into the prepared femur by passing the stem through sleeve 32 into the straight cavity formed in the medullary canal. As the stem moves into its final position, flutes 38 cut channels into the canal. As the last step in the implantation, the seem and sleeve 32 are locked together by applying a sharp impact force to the stem to engage tapered surface 26 with tapered surface 50.

The tapered surface(s) formed on stem 13 can have a variety of inclinations. For example, taper angles of 6° total included angle for surfaces 26 and 50 have been found to work successfully. Similar taper angles can be used for surfaces 28 and mating surfaces 52 and 56. Other taper angles which can be used are in the range of from about 3° to about 10°. For components made of a titanium alloy, preferred surfaces for the interlocking tapers are a smooth machined surface on the stem and a recrystallized surface on the sleeve's internal taper as occurs during sintering of a porous coating.

The components of the prosthesis can be constructed from surgically implantable materials such as chemically pure titanium or a titanium alloy containing 6% aluminum and 4% vanadium for stem 13, bone replacement element 54, and sleeves 32 and 34 (see ASTM Specification No. F136) and ultra high molecular weight polyethylene for element 64. When porous coating is used, the coating can comprise small spheres or particles of the same material as that used to form the underlying component.

Although specific embodiments of the invention have been described and illustrated, it is to be understood that modifications can be made without departing from the invention's spirit and scope. For example, although the invention has been illustrated in the context of a femoral prosthesis, it is also applicable to other artificial joints, such as, shoulder and knee joints. A variety of other modifications which do not depart from the scope and spirit of the invention will be evident to persons of ordinary skill in the art from the disclosure herein. The following claims are intended to cover the specific embodiments set forth herein as well as such modifications, variations, and equivalents.

What is claimed is:

1. A prosthesis for implantation in a bone which has an end for receiving the prosthesis and a medullary canal, said prosthesis comprising:

(a) a stem comprising an elongated body having a joint motion surface at one end and an outside surface extending away from said joint motion surface, said outside surface including a tapered portion, said tapered portion being conically shaped with a circular cross section;

(b) an elongated sleeve for fixation within an elongated cavity created in the bone at the end of the bone for receiving the sleeve, said sleeve including an outer surface for engagement with said cavity in the bone and an internal taper for locking engagement with the tapered portion, said internal taper being conically shaped with a circular cross section;

(c) an elongated bone replacement element having a longitudinal length; and (d) means for attaching the bone replacement element to the stem at a location between the joint motion surface and the sleeve, wherein (i) the elongated sleeve is spaced from the joint motion surface by a distance which is greater than the longitudinal length of the bone replacement element and (ii) the stem extends beyond the elongated sleeve by an amount sufficient for stabilizing engagement with the bone's medullary canal.

2. The prosthesis of claim 1 wherein the bone replacement element is composed of a material selected from the group consisting of bone, metal, plastic, or ceramic.

3. A prosthesis for implantation in a bone which has an end for receiving the prosthesis, said prosthesis comprising:

(a) a stem comprising an elongated body having a joint motion surface at one end and an outside surface extending away from said joint motion surface, said outside surface including a tapered portion, said tapered portion being conically shaped with a circular cross section;

(b) an elongated sleeve for fixation within an elongated cavity created in the bone at the end of the bone for receiving the sleeve, said sleeve including an outer surface for engagement with said cavity in the bone and an internal taper for locking engagement with the tapered portion, said internal taper being conically shaded with a circular cross section;

(c) a bone replacement element; and (d) means for attaching the bone replacement element to the stem at a location between the joint motion surface and the sleeve, said means comprising an internal taper for locking engagement with the tapered portion, said internal taper being conically shaped with a circular cross section and being formed on an inside surface of the bone replacement element.

4. A prosthesis for implantation in a bone which has an end for receiving the prosthesis, said prosthesis comprising:

(a) a stem comprising an elongated body having a joint motion surface at one end and an outside surface extending away from said joint motion surface, said outside surface including a first tapered portion, said first tapered portion being conically shaped with a circular cross section;

(b) an elongated sleeve for fixation within an elongated cavity created in the bone at the end of the bone for receiving the sleeve, said sleeve including an outer surface for engagement with said cavity in the bone and an internal taper for locking engagement with the first tapered portion, said internal taper being conically shaped with a circular cross section;

(c) a bone replacement element; and (d) means for attaching the bone replacement element to the stem at a location between the joint motion surface and the sleeve, wherein the outside surface of the stem includes a second tapered portion, said second tapered portion being located between the joint motion surface and the first tapered portion, the means for attaching comprises an internal taper for locking engagement with said second tapered portion, and said second tapered portion and said internal taper are each conically shaped with a circular cross section.

5. A prosthesis for implantation in a bone which has an end for receiving the prosthesis, said prosthesis comprising:

(a) a stem comprising an elongated body having a joint motion surface at one end and an outside surface extending away from said joint motion surface, said outside surface including a tapered portion, said tapered portion being conically shaped with a circular cross section;

(b) an elongated sleeve for fixation within an elongated cavity created in the bone at the end of the bone for receiving the sleeve, said sleeve including an outer surface for engagement with said cavity in the bone and an internal taper for locking engagement with the tapered portion, said internal taper being conically shaped with a circular cross section;

(c) a bone replacement element; and (d) means for attaching the bone replacement element to the stem at a location between the joint motion surface and the sleeve, wherein the outside surface of the stem includes flutes for engagement with the bone replacement element.

6. The prosthesis of claim 5 wherein the bone replacement element is composed of bone.

7. A prosthesis for implantation in a bone which has an end for receiving the prosthesis, said prosthesis comprising:

(a) a stem comprising an elongated body having a joint motion surface at one end and an outside surface extending away from said joint motion surface, said outside surface including a first tapered portion, said first tapered portion being conically shaped with a circular cross section;

(b) an elongated sleeve for fixation within an elongated cavity created in the bone at the end of the bone for receiving the sleeve, said sleeve including an outer surface for engagement with said cavity in the bone and an internal taper for locking engagement with the first tapered portion, said internal taper being conically shaped with a circular cross section;

(c) a bone replacement element; and (d) means for attaching the bone replacement element to the stem at a location between the joint motion surface and the sleeve, said means comprising a second sleeve affixed to the bone replacement element and attached to the stem, said second sleeve being a separate element from both said bone replacement element and said elongated sleeve.

8. The prosthesis of claim 7 wherein said second sleeve includes an internal taper and said second sleeve is attached to the stem through a locking engagement of the internal taper with the first tapered portion of the stem, said internal taper being conically shaped with a circular cross section.

9. The prosthesis of claim 7 wherein the outside surface of the stem includes a second tapered portion located between the joint motion surface and the first tapered portion, the second sleeve includes an internal taper and is attached to the stem through a locking engagement of the internal taper with the second tapered portion, and said second tapered portion and said internal taper are each conically shaped with a circular cross section.

10. The prosthesis of claim 9 wherein the outside surface of the stem includes flutes for engagement with the bone replacement element, said flutes being located between the first tapered portion and the second tapered portion.

11. The prosthesis of claim 7 wherein at least a portion of the outer surface of the second sleeve is stepped.

12. The prosthesis of claim 7 wherein at least a portion of the outer surface of the second sleeve is porous coated.

13. The prosthesis of claim 7 wherein the bone replacement element comprises a prepared bone graft having a cavity formed therein.

14. The prosthesis of claim 1 wherein at least a portion of the outer surface of the bone replacement element is porous coated.

15. The prosthesis of claim 1 wherein at least a portion of the outer surface of the elongated sleeve is porous coated.

16. The prosthesis of claim 1 wherein at least a portion of the outer surface of the elongated sleeve is stepped.

17. A prosthesis for implantation in a bone, said prosthesis comprising two prosthetic elements and a stem for attachment by locking tapers to the two prosthetic elements, said stem comprising an elongated body having a joint motion surface at one end and an outside surface extending away from said joint motion surface, said outside surface including an elongated tapered portion which has a sufficient length to permit attachment of the two prosthetic elements and which is conically shaped with a circular cross section for locking engagement with the two prosthetic elements, each of the two prosthetic elements having an internal taper which is conically shaped with a circular cross section.

18. A prosthesis for implantation in a bone, said prosthesis comprising a first prosthetic element, a second prosthetic element, and a stem for attachment by locking tapers to the first and second prosthetic elements, said stem comprising an elongated body having a joint motion surface at one end and an outside surface extending away from said joint motion surface, said outside surface including first and second elongated tapered portions each of which is conically shaped with a circular cross section, said first and second tapered portions being separated from one another along the length of the body, said first tapered portion being for locking engagement with the first prosthetic element and said second tapered portion being for locking engagement with the second prosthetic element, each of said two prosthetic elements having an internal taper which is conically shaped with a circular cross section.

19. The prosthesis of claim 18 wherein the outside surface of the stem includes flutes for engagement with one of the prosthetic elements, said flutes being located between the first and second tapered portions.

* * * * *